(12) United States Patent
Darling et al.

(10) Patent No.: US 8,994,538 B1
(45) Date of Patent: *Mar. 31, 2015

(54) SYSTEM, METHOD AND APPARATUS FOR MEDICAL DEVICE DATA REPORTING AND TAKING ACTION BASED THEREON

(71) Applicant: Instant Care, Inc., Vista, CA (US)

(72) Inventors: Richard Allen Darling, Poway, CA (US); George Joseph Seelman, Temecula, CA (US)

(73) Assignee: Instant Care, Inc., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/886,846

(22) Filed: May 3, 2013

Related U.S. Application Data

(63) Continuation-in-part of application No. 13/633,135, filed on Oct. 2, 2012, now abandoned.

(51) Int. Cl.
*G08B 23/00* (2006.01)
*G08B 21/02* (2006.01)

(52) U.S. Cl.
CPC ...................................... *G08B 21/02* (2013.01)
USPC ................. 340/573.1; 340/539.1; 340/539.12

(58) Field of Classification Search
CPC combination set(s) only.
See application file for complete search history.

(56) References Cited

U.S. PATENT DOCUMENTS 5,355,493 A * 10/1994 Silberbauer et al. .......... 717/136
2011/0202490 A1 * 8/2011 Gawlick .......................... 706/47

* cited by examiner

*Primary Examiner* — Travis Hunnings
(74) *Attorney, Agent, or Firm* — Thibault Patent Group

(57) ABSTRACT

A medical device data reporting system comprises: at least one medical device configured to output device data; a filter module configured to analyze the device data according to a predetermined criteria of parameters; an encoder module configured to encode the analyzed data into a digital format according to a predetermined encoding scheme and initiate a transmission of the encoded data; a transmitter module configured to transmit the encoded data to a location distal to the medical device via a telecommunication network; a digital receiver module located distal to the medical device configured to receive the digitally encoded data from the encoder module; and a decoder module configured to decode the digitally encoded data from the encoder module and communicate it to a responder capable of executing a predefined action sequence determined by the encoded data.

21 Claims, 5 Drawing Sheets

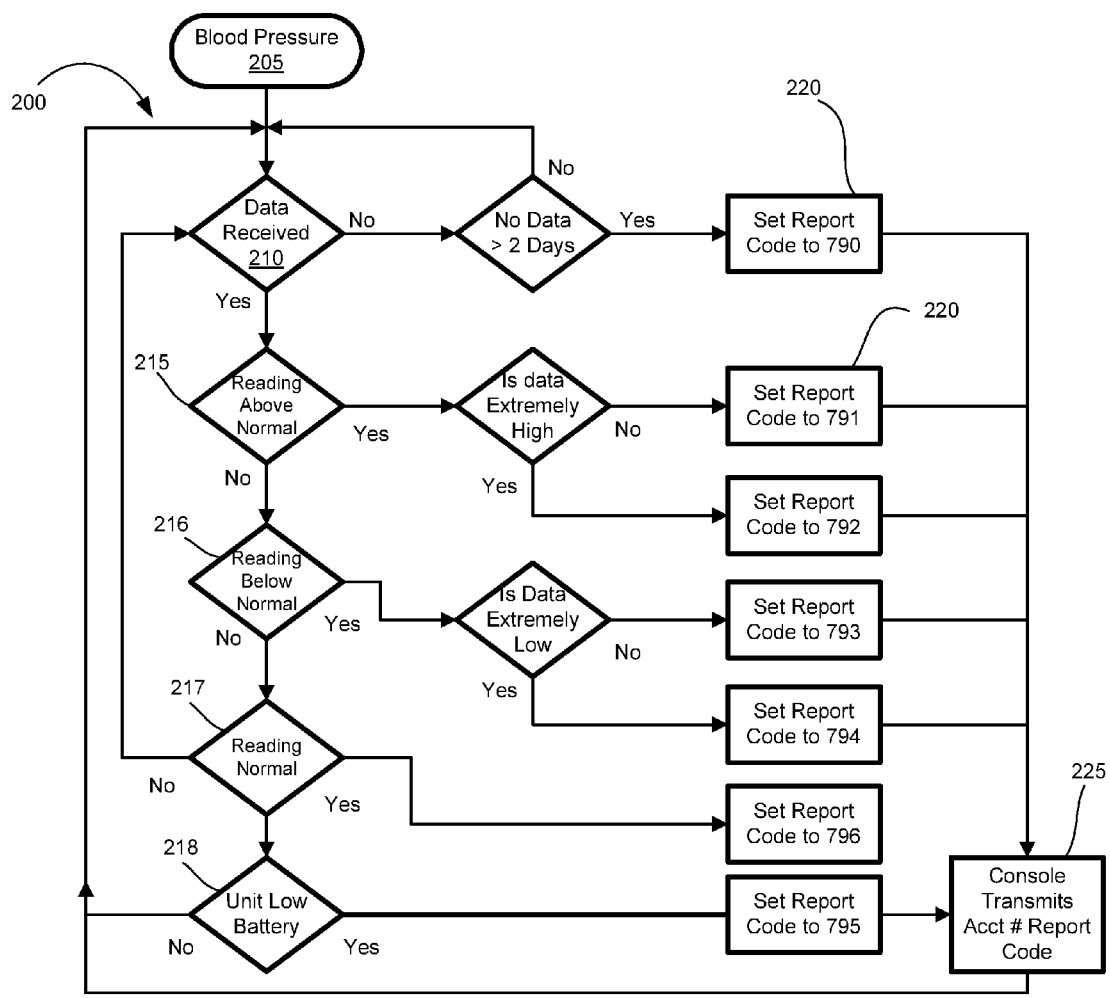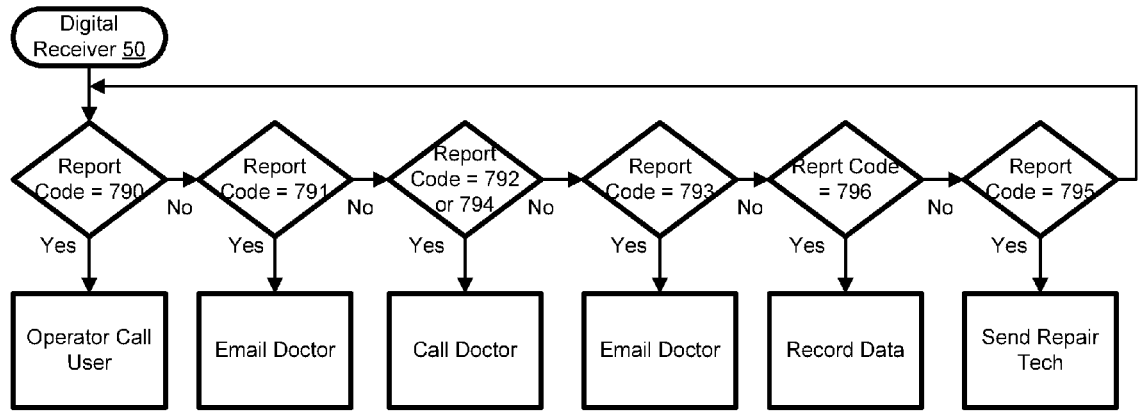
Fig. 2  RESPONDER 55

SYSTEM, METHOD AND APPARATUS FOR MEDICAL DEVICE DATA REPORTING AND TAKING ACTION BASED THEREON

CROSS-REFERENCES TO RELATED APPLICATIONS

This application is a continuation-in-part of U.S. application Ser. No. 13/633,135 filed Oct. 2, 2013, which is hereby incorporated herein by reference in its entirety.

BACKGROUND OF THE INVENTION

Currently data that is generated by medical devices can be processed in many different ways, but ultimately that data must be read and interpreted by medical professionals. This method is not only slow and time consuming, but it is also very costly.

It would be advantageous, therefore, to have a system that incorporates low level filters that prioritize and label the data for allowing processing of the data to be handled by low cost personnel who can take the appropriate action based on the data alert. This action could range from contacting medical professionals immediately or simply contacting the patient directly. This process removes the nuisance to the medical professionals of receiving non-critical alerts, while also prioritizing response levels to true medical emergencies. The present invention addresses these needs.

BRIEF SUMMARY OF EMBODIMENTS OF THE INVENTION (1) In a variant, a medical device data reporting system comprises: at least one medical device configured to output device data; a filter module in electrical communication with the medical device configured to analyze the medical device data according to a predetermined criteria parameters; an encoder module configured to encode the analyzed device data by the filter module into a digital format according to a predetermined encoding scheme and initiate a transmission of the encoded data; a transmitter configured to transmit the encoded data to a location distal to the medical device via a telecommunication network; a receiver module located distal to the medical device configured to receive the digitally encoded device data from the encoder module; and a decoder module configured to decode the digitally encoded device data and communicate it to a responder capable of executing a predefined action sequence determined by the encoded device data.

(2) In another variant, the encoded data is encoded according to a Contact ID protocol.

(3) In a further variant, the predetermined criteria of parameters and the predetermined encoding scheme are stored in memory in close proximity to the filter and the encoder.

(4) In still another variant, the predetermined criteria of parameters comprises a list of ranges of device data such that if a specific parameter falls within a particular range, the criteria for transmission is met, and the system sends the device data to the encoder to be encoded into a digital format.

(5) In yet a further variant, the predetermined criteria of parameters comprises a list of ranges of device data such that if a specific parameter falls within a normal or nominal reading, a transmission may or may not be sent based on user preference.

(6) In a variant, the telecommunication network is either one of a cellular network, a voice over internet protocol (VOIP) network, or a plain old telephone service (POTS).

(7) In another variant, the encoding scheme comprises a sequence of characters comprised of subsets of characters, wherein the subsets represent: an identification code; a predefined action sequence code; a device identifier code; and a code representing device data.

(8) In a further variant, the digital format comprises a frequency based format.

(9) In still another variant, a two way communication module housed in a unit containing the filter module, encoder module, and transmitter module and connected to the communication network; and wherein the predefined action sequence comprises one of: initiating a communication with medically trained personnel; initiating a communication with a device technician; initiating a communication with a person via the two way communication unit; and recording the device data.

(10) In yet a further variant, a unit for medical device data reporting, comprises: a filter module configured to analyze device data from a medical device and determine whether to initiate a transmission of the device data according to a predetermined criteria of parameters; an encoder module configured to encode the device data determined for transmission by the filter into module a digital format according to a predetermined encoding scheme and initiate a transmission of the encoded data; a transmitter module configured to transmit the encoded data to a location distal to the unit via a telecommunication network; and a non-transitory computer readable medium accessible by the filter module and the encoder module, having both (1) the predetermined criteria parameters and (2) the predetermined encoding scheme stored thereon.

(11) In a variant of the unit, the location distal to the medical device is a call center.

(12) In another variant of the unit, the encoded data is encoded according to Contact ID protocol.

(13) In a further variant of the unit, the location distal to the medical device is a medical center.

(14) In still another variant, a method for medical device data reporting, comprises: receiving data from at least one medical device configured to output device data; filtering medical device data by analyzing the device data and determining whether to initiate a transmission of the data according to a predetermined criteria of parameters; encoding device data determined for transmission by the filtering step into a digital format according to a predetermined encoding scheme; transmitting the encoded data to a location distal to the medical device via a telecommunication network; receiving the digitally encoded device data at a location distal to the medical device; and decoding the digitally encoded device data and communicating it to a responder capable of executing a predefined action sequence determined by the encoded device data.

(15) In a variant of the method, the encoding scheme is Contact ID.

(16) In another variant of the method, the predetermined criteria parameters comprises a list of ranges of device data such that if a specific parameter falls within a particular range, the criteria for transmission is met, the device data is encoded into a digital format and transmitted.

(17) In a further variant of the method, the encoded device data is sent over a telecommunication network comprising either one of a cellular network, a voice over internet protocol (VOIP) network or a plain old telephone service (POTS).

(18) In still another variant of the method, the location distal to the medical device is a call center.

(18) In yet a further variant of the method, the location distal to the medical device is a medical center.

(19) In a variant of the method, the predefined action sequence comprises one of: initiating a communication with medically trained personnel; initiating a communication with a device technician; and initiating a communication with a person via a two way communication unit proximal to the medical device.

(20) In another variant the method, the predefined action sequence comprises one of: initiating a communication with medically trained personnel; initiating a communication with a device technician; initiating a communication with a person via a two way communication unit proximal to the medical device; and recording the device data.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 2 is a flow chart of an example of a method of the medical device reporting system;

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 1:
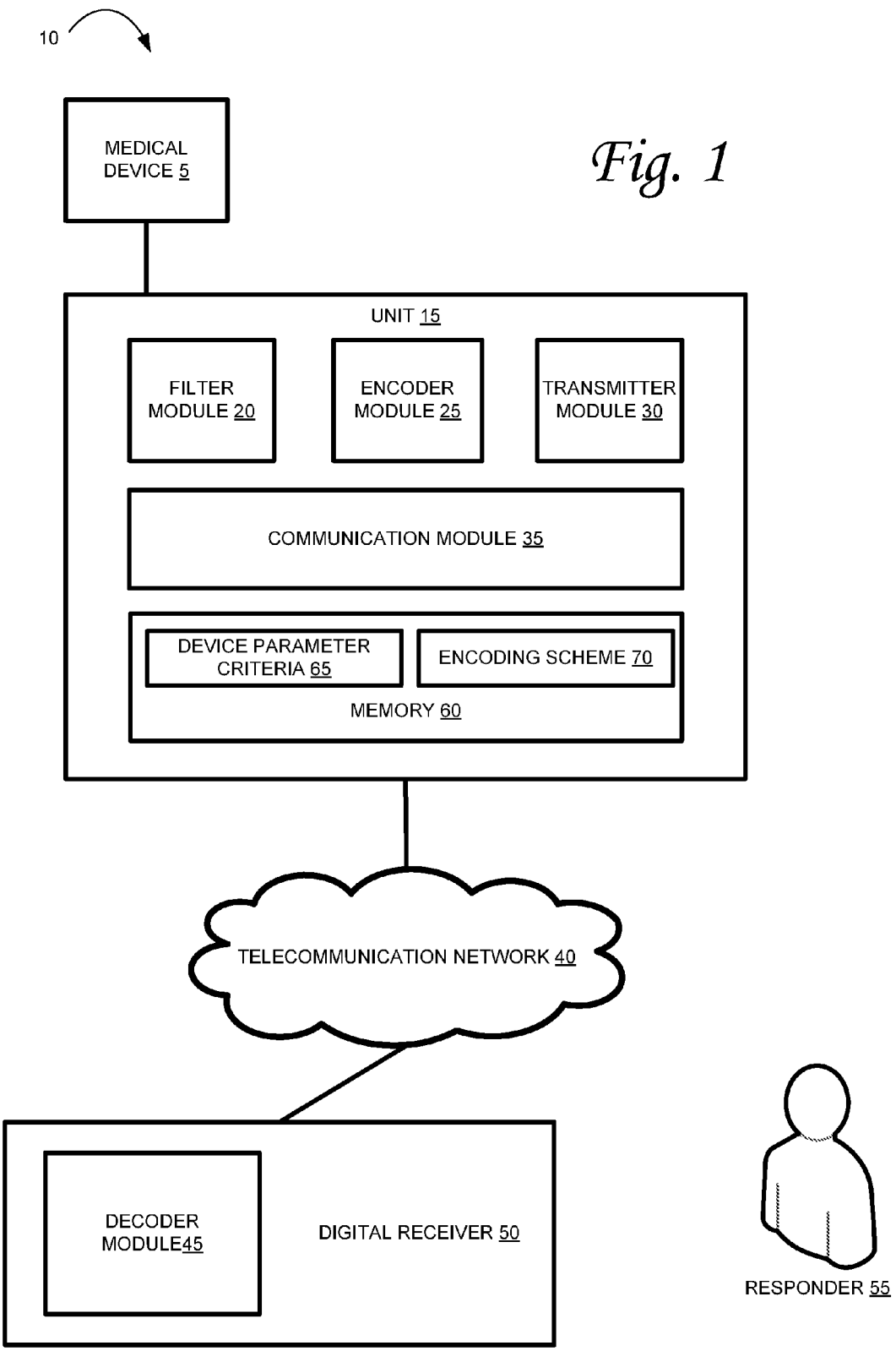
FIG. 1 is a block diagram of a variant of the medical device data reporting system.

The present invention is directed toward a system 10 and method for communicating medical data and alerts. In a variant, referring to FIG. 1, the medical device data reporting system 10 comprises at least one medical device 5 configured to output device data. In one example, device data may be blood pressure readings from a blood pressure monitor. In another example, device data may be data indicating the power state of the device as on or off. A filter module 20 is in electrical communication with the medical device 5 and is configured to analyze the device data according to a predetermined criteria of parameters. An encoder module 25 is configured to encode the device data analyzed by the filter module into a digital format according to a predetermined encoding scheme and initiate a transmission of the encoded data. A transmitter 30 is configured to transmit the encoded data to a location distal to the medical device via a telecommunication network, such as a POTS, voice over internet protocol (VOIP), or a cellular network.

Figure 5:
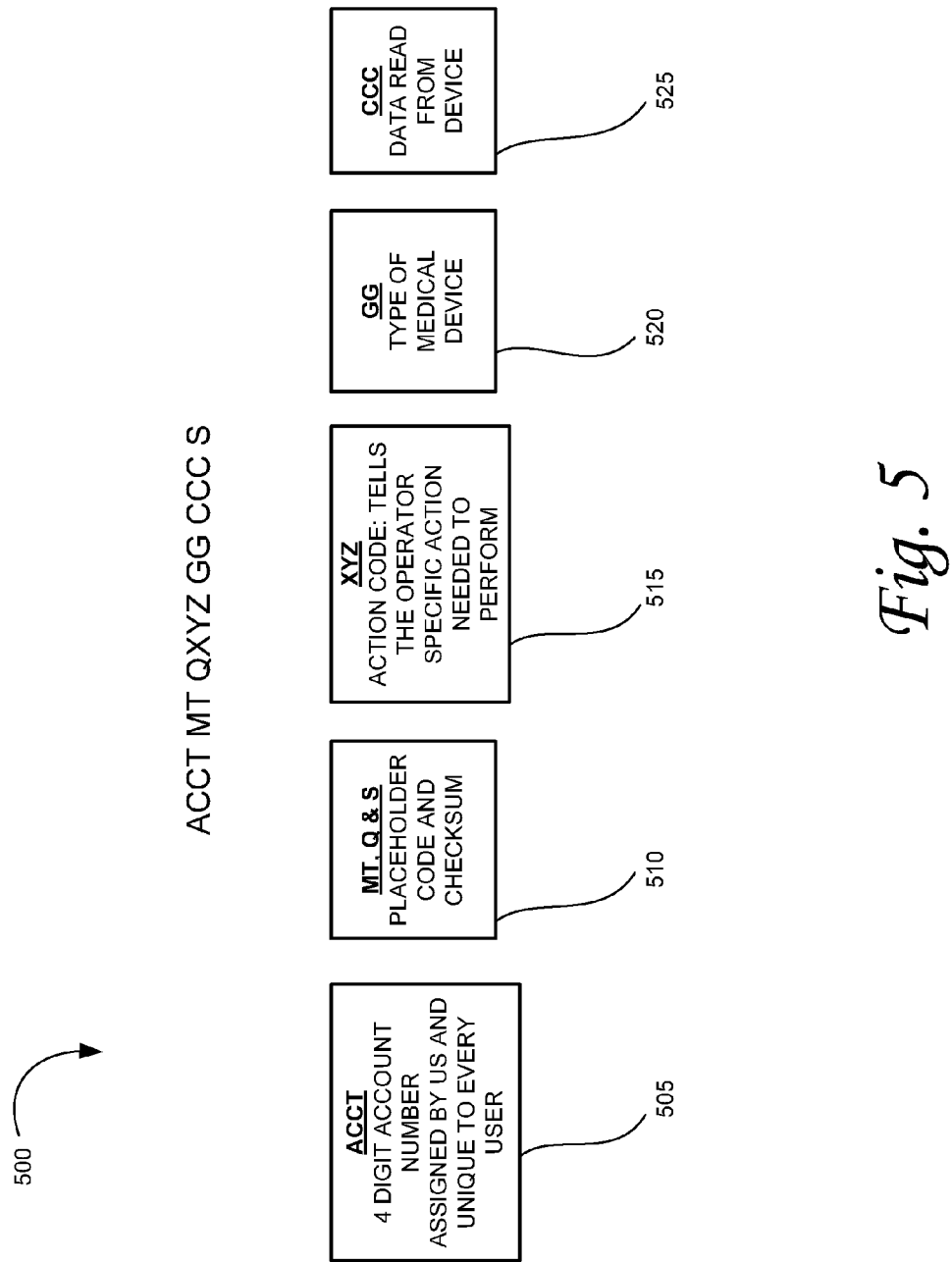
FIG. 5 is a block diagram illustrating an encoding scheme.

Optionally, the encoded data is encoded according to Contact ID. Referring to FIG. 5, the encoding scheme comprises a sequence of characters comprised of subsets of characters, wherein the subsets represent: an identification code 505; a predefined action sequence code 515; a device identifier 520 code; and a code representing device data 525. Contact ID requires data to be transmitted as a 16 digit code, ACCT-MTQXYZGGCCCS. In one example, the identification code 505 is represented by the characters occupying ACCT; the predefined action sequence code 515 is represented by the characters occupying XYZ; the device identifier 520 code is represented by the characters occupying GG; the code representing device data 525 is represented by the characters occupying CCC and optional data may is represented by the characters occupying MT and S represents a checksum character.

Optionally, a two-way communication module 35 is provided and, in a variant, the filter 20, encoder 25, transmitter 30 and two way communication module 35 are housed together in single hardware unit 15. A digital receiver 50 is located distal to the medical device and is configured to receive the digitally encoded device data. A decoder module 45 is configured to decode the digitally encoded device data and communicate it to a responder 55 capable of executing a predefined action sequence determined by the encoded device data.

In one example application 200 of the medical device data reporting system, referring to FIG. 2, a medical device comprises a blood pressure monitor 205, connected to the filter 20 either wirelessly or via a wired connection. The filter module 20 analyzes the data for one or more issues. For example, whether a reading is not received 210 for a predetermined period, such as 2 days; whether the reading is higher 215 or lower 216 than a predetermined threshold; whether the reading is within normal operating parameters 217; whether a reading is extremely high or low; whether a wireless unit has a low battery 218. If any of the above conditions are satisfied, the data is encoded 220 by an encoder 25 into a digital format with a report code to uniquely identify the condition. The report code may comprise a three-digit code, or any digital code suitable for handling by the communication system. In FIG. 2, report codes of 790, 791, 792, 793, 794, 795, and 796 represent, respectively, no data received for least 5 days, the data falls above a predetermined range, the data falls very far above a predetermined range, the data falls below a predetermined range, the data falls very far below a predetermined range, the medical device battery is low, the data falls within a predetermined or normal range of values.

The encoded data is then sent 225 off site to a digital receiver 50 where a responder 55 reads the report code and an account number associated with the medical device. Optionally, the responder comprises a person trained to follow an action pattern or sequence that falls generally into three categories of actions: initiating a communication with medically trained personnel, for example calling a licensed physician; initiating a communication with a device technician, for example calling a technician trained to repair or operate the medical device; initiating a communication with a person at the location of the medical device, for example, a patient being monitored by the medical device, via standard communication channels such as telephones or, optionally, via the two way communication module 35.

Optionally a fourth category of the predefined action sequence may comprise recording the device data, either automatically through a computing device or manually by a human responder. Optionally, the responder may comprise a robot or automated response system, configured to initiate a communication to any one of the medical professional, technician or person at the location of the medical device, based on the report code.

Upon receiving the report code, responder executes a predefined action sequence based on the report code. In the example application illustrated in FIG. 2, if a report code of 790 is receiving which indicates no data received for 5 days, then a prescribed action sequence dictates the responder 55 to call the location of the medical device. If a report code of 791 is received which indicates a device reading that falls above a predetermined range, and then a prescribed action sequence dictates the responder 55 to email a medical professional. If a report code of 792 is received which indicates a device reading that falls very far above a predetermined range, and then a prescribed action sequence dictates the responder 55 to call a medical professional, which would elicit a quicker response from the medical professional than email would. If a report code of 793 is received which indicates a device reading that falls below a predetermined range, and then a prescribed action sequence dictates the responder 55 to email a medical professional. If a report code of 794 is received which indicates a device reading that falls very far below a predetermined range, and then a prescribed action sequence dictates the responder 55 to call a medical professional, which would elicit a quicker response from the medical professional than email would. If a report code of 796 is received which indicates a device reading that falls within normal standard operating parameters for the device, and then a prescribed action sequence dictates the responder 55 to do nothing and let the system record the time and data or the responder can manually record the data. If a report code of 795 is received which indicates a low battery lever on the device, and then a prescribed action sequence dictates the responder 55 to contact a device technician to service the device.

In another variant of the system, the predetermined criteria of device parameters and the predetermined encoding scheme are stored in memory in close proximity to the filter module and the encoder module, for example, in the unit 15. The parameters determine which data should be selected for encoding a communication off-site. The predetermined encoding scheme determines what code to assign to a specific data, for example, report code 795 to represent a low battery level data from the device 5.

In a further variant of the system, the predetermined criteria of parameters comprise a list of ranges of device data such that if a specific parameter falls within a particular range, the criteria for transmission is met, and the system sends the device data to the encoder to be encoded into a digital format.

In another variant, the predetermined criteria of parameters comprises a list of ranges of device data such that if a specific parameter falls within a normal or nominal reading a transmission may or may not be sent based on a user preference.

In still another variant of the system, the telecommunication network is either one of a cellular network, a voice over internet protocol (VOIP) or a plain old telephone service (POTS).

In yet a further variant of the system, the digital format comprises a sound based format, for example dual-tone multi-frequency signaling (DTMF).

In a variant of the system, a two way communication module is housed in a unit 15 containing the filter 20, encoder 25, and transmitter 30 and is connected to the communication network 40. The predefined action sequence comprises one of: initiating a communication with medically trained personnel; initiating a communication with a device technician; initiating a communication with a person via the two way communication unit; and recording the device data.

In another variant, a unit 15 for medical device data reporting comprises: a filter module 20 configured to analyze device data from a medical device 5 according to a predetermined criteria of parameters. An encoder 25 is configured to encode the device data into a digital format according to a predetermined encoding scheme and initiate a transmission of the encoded data. A transmitter 30 is configured to transmit the encoded data to a location distal to the unit via a telecommunication network 40. Optionally, the network may be public or private and may be a dedicated network, install specifically with the system 10. A non-transitory computer readable medium 60 is accessible by the filter 20 and the encoder 25, has both (1) the predetermined criteria of device parameters and medical data and (2) the predetermined encoding scheme stored thereon. Optionally, the unit has a two-way communication module 35. Optionally, the two-way communication module 35 comprises an audio receiver and an audio transmitter.

Figure 3:
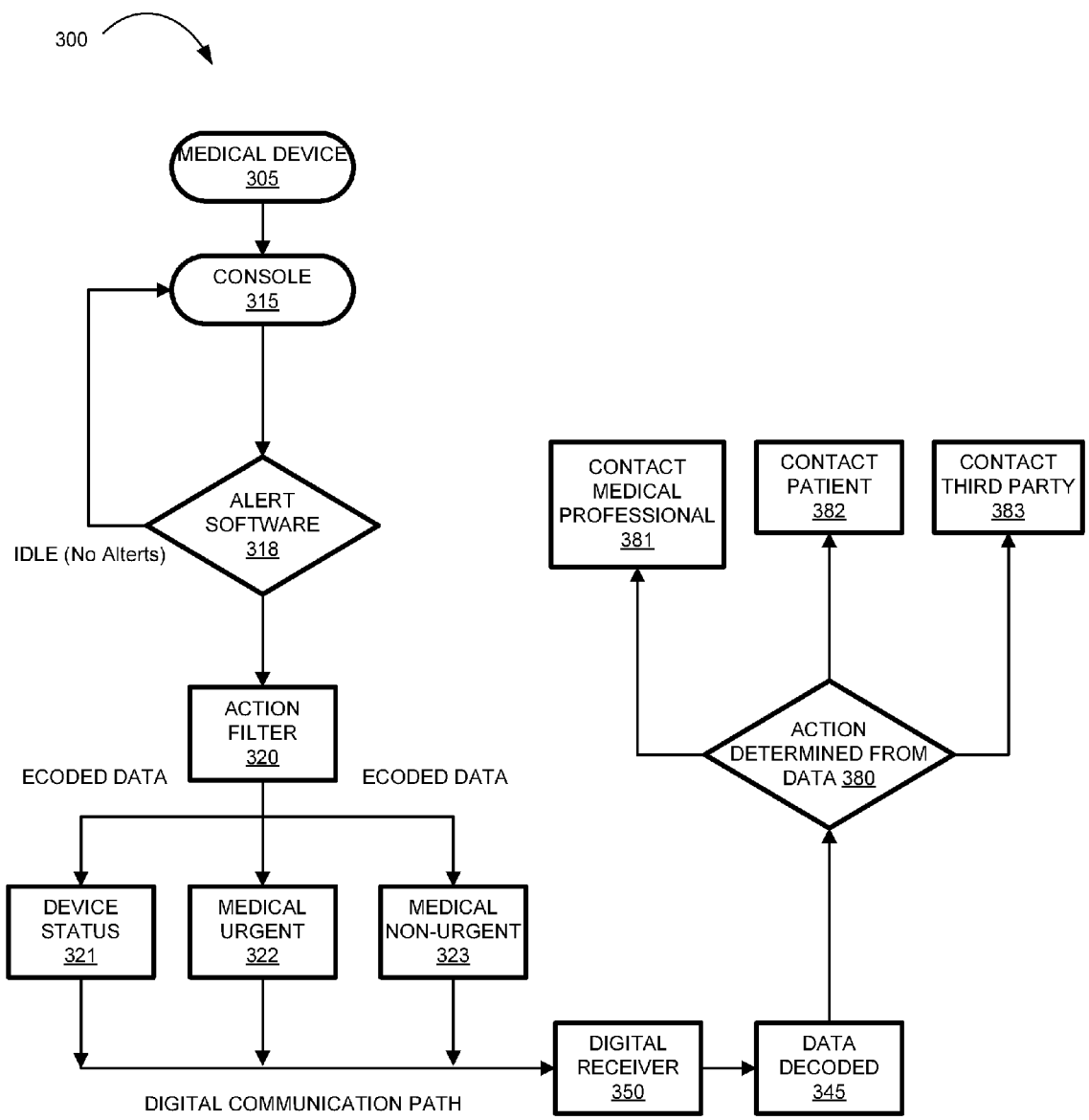
FIG. 3 is a block diagram of a variant the medical device data reporting system.

In a variant, FIG. 3 provides a high level overview of the system 300. A medical device 305 operating at a patient's home or location, is monitored by a console 315 having console software 318 operating thereon. The console checks for and reads device data from the medical device. Data received by the console 315 is sent through an action filter 320, which determines whether to encode data and communicate data off-site. If the data is determined by the action filter 320 to be sent off site, based on predetermined criteria, the data is encoded by the console into, optionally, three categories of data, comprising device status 321 (low battery level, for example), data that calls for non-urgent medical attention 322 and data that calls for urgent medical attention 323. The encoded data is sent to a receiver 350, where the data is decoded by a decoder 345. A digital receiver 350 displays customer information from the transmitted account number and report code. A responder 55 then takes the appropriate action based on that report code. A responder 55 may be configured to act on the data in, optionally, three types of predefined actions 380, comprising: Contacting a medical professional either urgently or non-urgently 381, contacting the patient 382 and contacting a third party 382. A third party may be contacted, for example, to service the medical device.

Optionally, the unit encodes the data according to Contact ID protocol. Optionally, the unit transmits the encoded data to a location distal to the unit via a telecommunication network, wherein the location distal to the medical device is a medical center.

Figure 4:
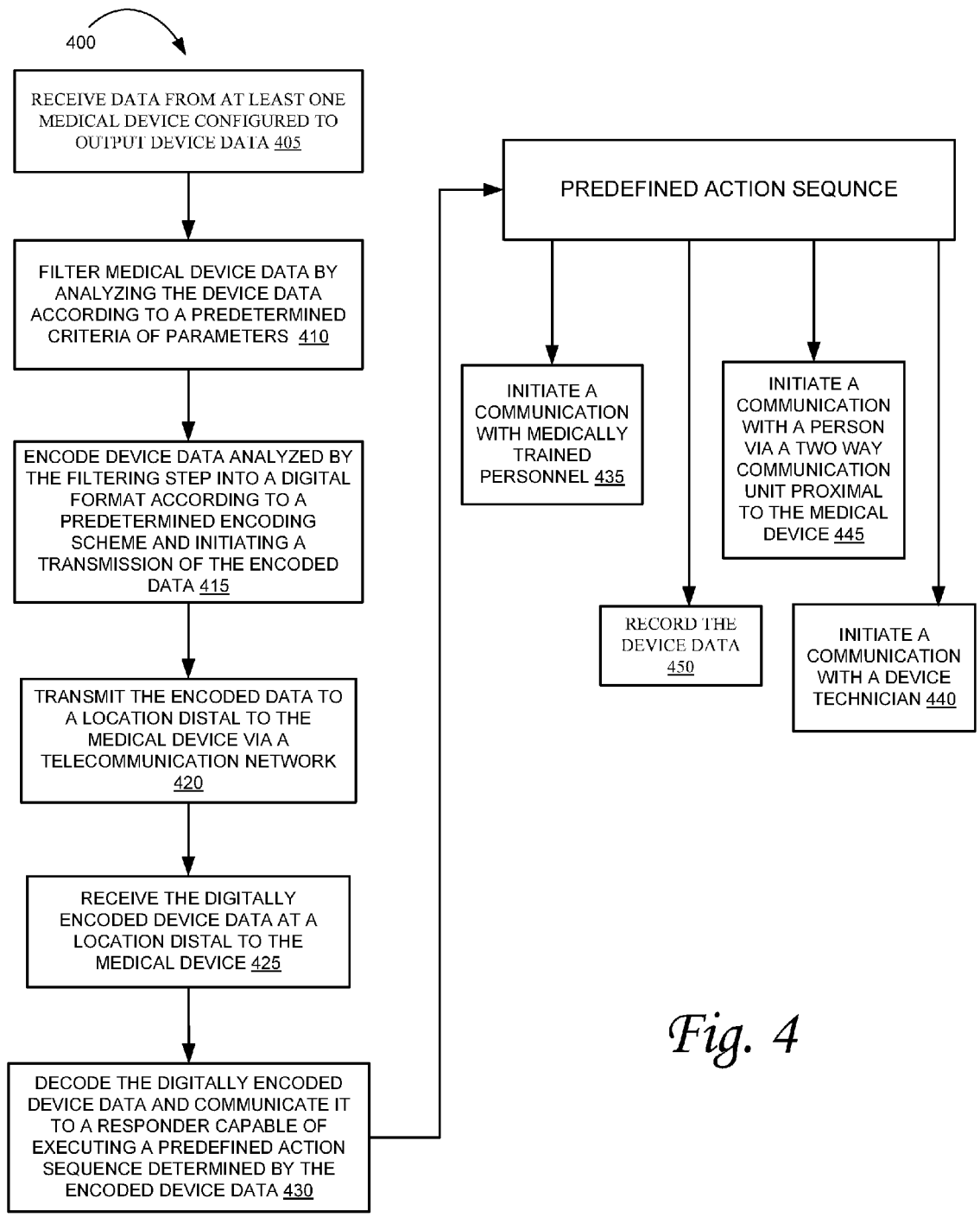
FIG. 4 is a flow chart of a method of the medical device reporting system.

In yet a further variant, referring to FIG. 4, a method 400 for medical device data reporting, comprises: receiving 405 data from at least one medical device configured to output device data; filtering 410 medical device data by analyzing the medical device data according to a predetermined criteria of parameters; encoding 415 device data analyzed by the filtering step into a digital format according to a predetermined encoding scheme and initiating a transmission of the of the encoded data; transmitting 420 the encoded data to a location distal to the medical device via a telecommunication network; receiving 425 the digitally encoded device data from the encoder step at a location distal to the medical device; and decoding 430 the digitally encoded device data and communicating it to a responder capable of executing a predefined action sequence determined by the encoded device data.

In a variant of the method, the predetermined criteria of parameters and the predetermined encoding scheme are read from a non-transitory computer readable medium in close proximity to the medical device.

In another variant of the method, the predetermined criteria of parameters comprises a list of ranges of device data such that if a specific parameter falls within a particular range, the criteria for transmission is met, the device data is encoded into a digital format and transmitted.

In a further variant of the method, the encoded device data is sent over a telecommunication network comprising either one of a cellular network, a VOIP network or a plain old telephone service (POTS).

In yet another variant of the method, the digital format comprises a sound based format. Optionally, the data is encoded according to Contact ID protocol. Optionally, the encoded data is transmitted to a location distal to the unit via a telecommunication network, wherein the location distal to the medical device is a medical center.

In yet another variant of the method, the digital format comprises a frequency-based format, such as at infrasound, ultrasound frequencies or other frequencies mediums such as electrical over a network.

In still a further variant of the method, referring to FIG. 4, the predefined action sequence comprises one of: initiating 435 a communication with medically trained personnel; initiating 440 a communication with a device technician; and initiating 445 a communication with a person via a two way communication unit proximal to the medical device.

In a variant of the method, referring to FIG. 4, the predefined action sequence comprises one of: initiating 435 a communication with medically trained personnel; initiating 440 a communication with a device technician; and initiating 445 a communication with a person via a two way communication unit proximal to the medical device; and recording 450 the device data.

Previous methods used to send medical data are very costly and require a medical professional to read and interpret that information. By using the 16 character Contact ID based encoding scheme described herein, one is able to take a wide range of medical information generated by any medical device and convert that data into the 16 character encoded data. Because of the 16 character encoding scheme, one can utilize the transmit and receive Contact ID format.

The Contact ID format allows one to read, filter and transmit critical data that does not require a costly medical professional to read it. The encoding scheme described herein is structured so that one can decode on the receive side and label the information in a manner that allows it to be handled by low cost personnel.

Current delivery methods require that a medical professional read through all messages and determine which ones need to be addressed and in which order. This is incredibly time consuming and is a major part of why health care costs are so high. By filtering and labeling the data for the medical professional in advance, the present invention expedites patient care and immediately addresses a priority level for every message received in real time. The method of the present invention utilizes the medical professional's time in the most efficient manner, generates better health outcomes for the patient and greatly reduces the cost of delivering a multitude of medical data.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A medical device data reporting system, comprising:
   at least one medical device configured to monitor a person and output device data;
   a filter module configured to analyze the medical device data according to a predetermined criteria parameters;
   an encoder module configured to encode the analyzed device data by the filter module into a digital format according to a predetermined encoding scheme and initiate a transmission of the encoded data, the encoding scheme configured to assign one of a plurality of predefined action sequence codes to the encoded data based on the device data, each of the predefined action sequence codes indicating a respective action to be taken by a remote responder;
   a transmitter configured to transmit the encoded data to a location distal to the medical device via a telecommunication network;
   a receiver module located distal to the medical device configured to receive the digitally encoded device data from the encoder module; and
   a decoder module configured to decode the digitally encoded device data and communicate the assigned one of the predefined action sequence codes to the responder for execution by the responder.

2. The system of claim 1, wherein the predefined action sequence codes each comprise a Contact ID code from a Contact ID protocol.

3. The system of claim 1, wherein the predetermined criteria of parameters and the predetermined encoding scheme are stored in memory in close proximity to the filter and the encoder.

4. The system of claim 1, wherein the predetermined criteria of parameters comprises a list of ranges of device data such that if a specific parameter falls within a particular range, the criteria for transmission is met, and the system sends the device data to the encoder to be encoded into a digital format.

5. The system of claim 1 wherein the predetermined criteria of parameters comprises a list of ranges of device data such that if a specific parameter falls within a normal or nominal reading, a transmission may or may not be sent based on user preference.

6. The system of claim 1, wherein the encoding scheme comprises a sequence of characters comprised of subsets of characters, wherein the subsets represent:
   an identification code;
   the predefined action sequence code;
   a device identifier code; and
   a code representing device data.

7. The system of claim 1, wherein the digital format comprises a frequency based format.

8. The system of claim 1, wherein the each of the plurality of predefined action sequence codes indicates one of the following actions:
   initiating a communication with medically trained personnel;
   initiating a communication with a device technician; or
   initiating a communication with the person.

9. The system of claim 1, wherein the each of the plurality of predefined action sequence codes indicates one of the following actions:
   initiating a communication with medically trained personnel;
   initiating a communication with a device technician; or
   initiating a communication with the person.

10. A unit for medical device data reporting, comprising:
    a filter module configured to analyze device data from a medical device that monitors a person and determine whether to initiate a transmission of the device data according to a predetermined criteria of parameters;
    an encoder module configured to encode the device data determined for transmission by the filter into a digital format according to a predetermined encoding scheme and initiate a transmission of the encoded data, the encoding scheme configured to assign one of a plurality of predefined action sequence codes to the encoded data based on the device data, each of the predefined action sequence codes indicating a respective action to be taken by a remote responder;
    a transmitter module configured to transmit the encoded data to a location distal to the unit via a telecommunication network for execution of the assigned one of the plurality of predefined action sequence codes; and
    a non-transitory computer readable medium accessible by the filter module and the encoder module, having both (1) the predetermined criteria parameters and (2) the predetermined encoding scheme stored thereon.

11. The unit of claim 10, wherein the location distal to the medical device is a call center.

12. The unit of claim 10, wherein each of the predefined action sequence codes comprise a Contact ID code from a Contact ID protocol.

13. The apparatus of claim 10 wherein the predetermined criteria of parameters comprises a list of ranges of device data such that if a specific parameter falls within a normal or nominal reading, a transmission may or may not be sent based on user preference.

14. A method for medical device data reporting of a person, comprising:
- receiving data from at least one medical device that is monitoring the person and configured to output device data;
- filtering medical device data by analyzing the device data and determining whether to initiate a transmission of the data according to a predetermined criteria of parameters;
- encoding the device data determined for transmission by the filtering step into a digital format according to a predetermined encoding scheme, the encoding scheme configured to assign one of a plurality of predefined action sequence codes to the encoded data based on the device data, each of the predefined action sequence codes indicating a respective action to be taken by a remote responder;
- transmitting the encoded data to a location distal to the medical device;
- receiving the digitally encoded device data at the location distal to the medical device; and
- decoding the digitally encoded device data and communicating the assigned one of the predefined action sequence codes to the responder for execution by the responder.

15. The method of claim 14, wherein each of the predefined action sequence codes comprise a Contact ID code from a Contact ID protocol.

16. The method of claim 14, wherein the predetermined criteria parameters comprises a list of ranges of device data such that if a specific parameter falls within a particular range, the criteria for transmission is met, the device data is encoded into a digital format and transmitted.

17. The method of claim 14, wherein the encoded device data is sent over an existing telecommunication network comprising either one of a cellular network, a voice over internet protocol (VOIP) network or a plain old telephone service (POTS).

18. The method of claim 14, wherein the location distal to the medical device is a call center.

19. The method of claim 14, wherein the predefined action sequence comprises one of:
- initiating a communication with medically trained personnel;
- initiating a communication with a device technician; and
- initiating a communication with the person.

20. The method of claim 14, wherein initiating a communication with the person comprises initiating communication via a two-way communication unit proximal to the medical device.

21. The method of claim 14 wherein the predetermined criteria of parameters comprises a list of ranges of device data such that if a specific parameter falls within a normal or nominal reading, a transmission may or may not be sent based on user preference.

* * * * *